United States Patent [19]
Deters et al.

[11] Patent Number: 4,837,111
[45] Date of Patent: Jun. 6, 1989

[54] DOSAGE FORM FOR DISPENSING DRUG FOR HUMAN THERAPY

[75] Inventors: Joseph C. Deters, Mountain View; Patrick S. L. Wong, Hayward; Brian L. Barclay, Sunnyvale; Felix Theeuwes, Los Altos; David R. Swanson, Palo Alto, all of Calif.

[73] Assignee: ALZA Corporation, Palo Alto, Calif.

[21] Appl. No.: 173,524

[22] Filed: Mar. 21, 1988

[51] Int. Cl.$^4$ .............................................. A61K 9/24
[52] U.S. Cl. .................................... 424/473; 424/430; 424/436
[58] Field of Search ......................................... 424/473

[56] References Cited

U.S. PATENT DOCUMENTS

| | | |
|---|---|---|
| 3,845,770 | 11/1974 | Theeuwes et al. .................. 128/260 |
| 3,916,899 | 11/1975 | Theeuwes et al. .................. 128/260 |
| 4,111,202 | 9/1978 | Theeuwes ............................ 128/260 |
| 4,235,236 | 11/1980 | Theeuwes ............................ 128/260 |
| 4,309,996 | 1/1982 | Theeuwes ............................ 128/260 |
| 4,320,759 | 3/1982 | Theeuwes ............................ 128/260 |
| 4,532,135 | 7/1985 | Edwards ........................... 514/223.2 |
| 4,758,569 | 7/1988 | Swindell ............................ 514/254 |
| 4,760,057 | 8/1988 | Alexander ......................... 514/254 |
| 4,765,989 | 8/1988 | Wong et al. ........................ 424/473 |

Primary Examiner—Thurman K. Page
Assistant Examiner—L. R. Horne
Attorney, Agent, or Firm—Paul L. Sabatine; Edward L. Mandell; Steven F. Stone

[57] ABSTRACT

An osmotic dosage system is disclosed for delivering the therapeutically beneficial drug doxazosin to an environment of use over time.

10 Claims, 6 Drawing Sheets

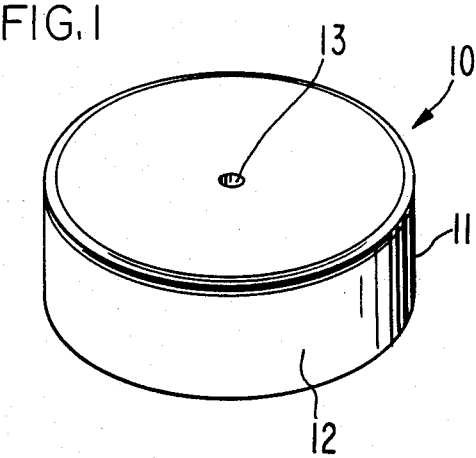
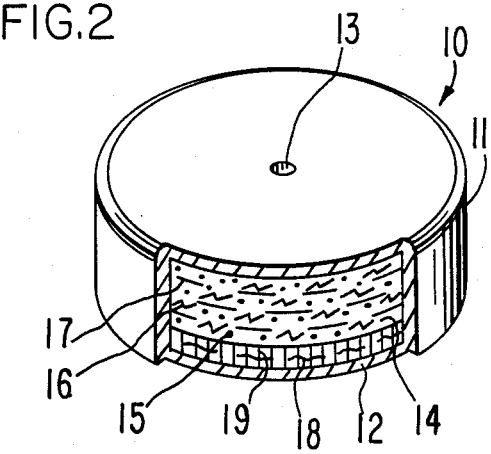
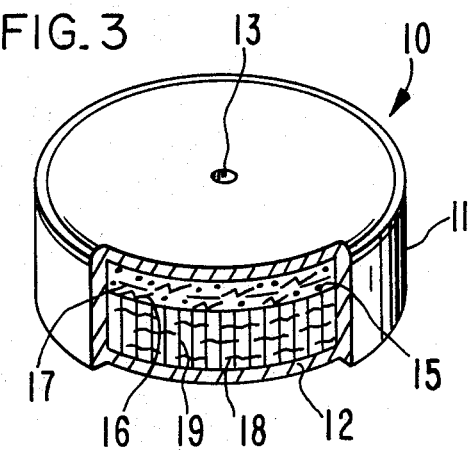
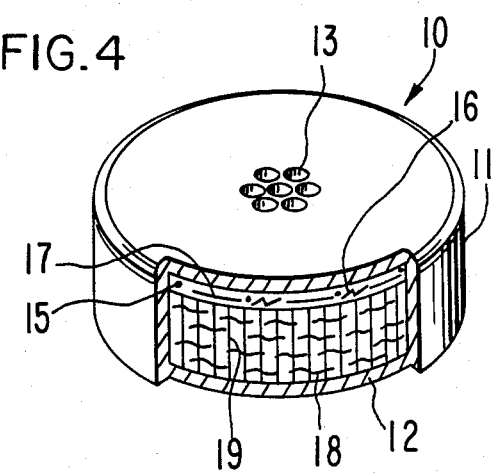
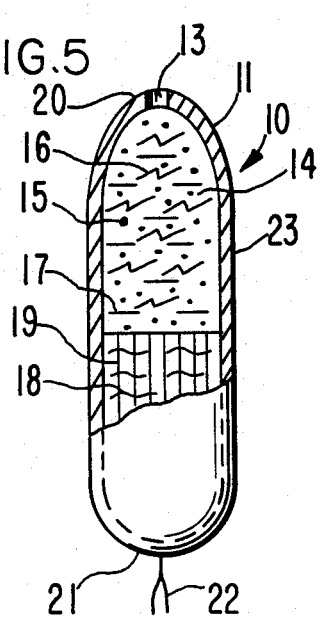
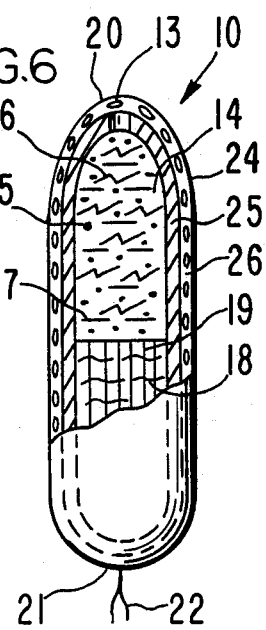
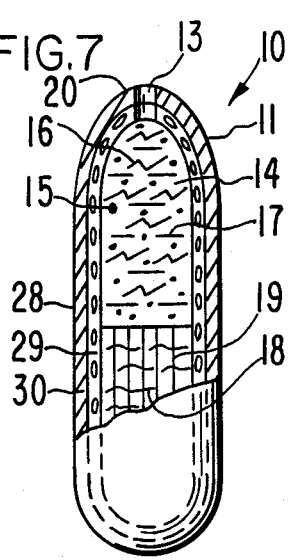

DOSAGE FORM FOR DISPENSING DRUG FOR HUMAN THERAPY

CROSS-REFERENCE TO RELATED APPLICATION

This application is copending with U.S. Pat. Appln. Ser. No. 902,915 filed Sept. 2, 1986, now U.S. Pat. No. 4,765,989 and with U.S. Pat. Appln. Ser. No. 912,712 filed Sept. 29, 1986 now U.S. Pat. No. 4,783,337 which applications are incorporated herein by reference. These applications are assigned to ALZA Corporation of Palo Alto, Calif.

FIELD OF THE INVENTION

This invention pertains to both a novel and unique delivery system. More particularly, the invention relates to an osmotic device comprising a wall comprising in at least a part a semipermeable material that surrounds a compartment comprising: (1) a first osmotic composition comprising a beneficial agent, and an osmopolymer and optionally an osmagent, said composition in contacting arrangement with (2) a second composition comprising an osmopolymer and optionally an osmagent. At least one passageway through the wall connects the exterior of the osmotic device with the first osmotic composition containing the beneficial agent for delivering the beneficial agent from the osmotic device. The osmotic device is preferably useful for delivering (3) beneficial agents that because of their solubilities are difficult to deliver in a known amount at a controlled rate from an osmotic dispensing system, and for delivering (4) beneficial agents that are therapeutically very active and are dispensed in small amounts at a controlled rate from the osmotic dispensing system.

BACKGROUND OF THE INVENTION

Since the beginning of antiquity both pharmacy and medicine have sought a delivery system for administering a beneficial drug. The first written reference to a delivery system is in the Eber Papyrus, written about 1552 B.C. The Eber Payrus mentions delivery systems such as anal suppositories, vaginal pessaries, ointments, oral pill formulations, and other delivery systems. About 2500 years passed without any advance in dosage form development, when the Arab physician Rhazes, 865–925 A.D., invented the coated pill. About a century later the Persian Avicenna, 980–1037 A.D., coated pills with gold or silver for increasing patient acceptability and for enhancing the effectiveness of the drug. Also around this time, the first tablet was described in Arabian manuscripts written by al-Zahrawi, 936–1009 A.D. The manuscripts described a tablet formed from the hollow impressions in two facing tablet molds. Pharmacy and medicine waited about 800 years for the next innovation in delivery systems when, in 1883, Mothes invented the capsule for administering drug. The next quantum leap in dosage forms came in 1972 with the invention of the osmotic delivery system by inventors Theeuwes and Higuchi as disclosed in U.S. Pat. Nos. 3,845,770 and 3,916,899.

The osmotic system disclosed in those patents comprises a semipermeable wall that surrounds a compartment containing a useful agent. The wall is permeable to the passage of an external fluid, and it is substantially impermeable to the passage of useful agent. There is at least one passageway through the wall for delivering the useful agent from the osmotic system. These systems release a useful agent by fluid being imbibed through the semipermeable wall into the compartment at a rate determined by the permeablility of the semipermeable wall and the osmotic pressure gradient across the semipermeable wall to produce an aqueous solution containing useful agent that is dispensed through the passageway from the system. These systems are extraordinarily effective for delivering a useful agent that is soluble in the fluid and exhibits an osmotic pressure gradient across the semipermeable wall against the external fluid.

A pioneer advancement in osmotic delivery systems, manufactured in the form of an osmotic dosage form, was presented to the dispensing arts by inventor Felix Theeuwes in U.S. Pat. No. 4,111,202. In this patent, the delivery kinetics of the osmotic device is enhanced for delivering useful agents, including drugs, that are insoluble to very soluble in the fluid, by manufacturing the osmotic device with a useful agent compartment and an osmagent compartment separated by an internal film. The internal film is movable from a rested to an expanded state. The osmotic device delivers agent by fluid being imbibed through the semipermeable wall into the osmagent compartment producing a solution that causes the compartment to increase in volume and act as a driving force that is applied against the film. This force urges the film to expand in the device against the useful agent compartment and correspondingly diminish the volume of the useful agent compartment, whereby useful agent is dispensed through the passageway from the osmotic device. While this device operates successfully for its intended use, and while it can deliver numerous useful agents of varying solubilities, its use can be limited because of the manufacturing steps and costs needed for fabricating and placing the movable film in the compartment of the osmotic device.

In U.S. Pat. No. 4,327,725 patentees Richard Cortese and Felix Theeuwes provided an osmotic dispensing device for delivering beneficial agents, that because of their solubilities in aqueous and biological fluids, are difficult to deliver in meaningful amounts at controlled rates over time. The osmotic devices of this patent comprise a semipermeable wall surrounding a compartment containing a beneficial agent that is insoluble to very soluble in aqueous and biological fluids, and an expandable hydrogel. In operation the hydrogel expands in the presence of external fluid that is imbibed into the device thereby dispensing the beneficial agent through the passageway from the device. This device operates successfully for its intended use, and it delivers many difficult to deliver beneficial agents for their intended purpose. Now it has been observed its use can be enhanced by using a pair of hydrogels neat or, optionally, mixed with an osmagent for providing maximum self-expansion for urging all beneficial agents from the device.

It will be appreciated by those versed in the dispensing art, that if an osmotic device can be provided that exhibits a high level of osmotic activity, such an osmotic device would have a positive value and represent an advancement in the dispensing art. Likewise, it will be immediately appreciated by those versed in the dispensing art that if an osmotic device is made available possessing dual thermodynamic osmotic activity for delivering increased amounts of a beneficial agent, said osmotic device would find practical application in the fields of pharmacy and medicine.

OBJECT OF THE INVENTION

Accordingly, in view of the above presentation, it is an immediate object of this invention to provide an osmotic system that can be manufactured by standard manufacturing techniques into osmotic devices of various sizes, shapes and forms that represent a further improvement and advancement in the dispensing art.

Another object of the invention is to provide an osmotic system manufactured in the form of an osmotic device for delivering in vivo a beneficial drug that is difficult to deliver and now can be delivered by the osmotic device provided by this invention in therapeutically effective amounts over time.

Another object of the invention is to provide an osmotic system possessing dual osmotic activity that operates as an integrated unit, which system comprises a compartment containing a first osmotic composition comprising a drug, and preferably an osmopolymer and/or an osmagent, and a second osmotic composition comprising an osmopolymer and an optional osmagent, with the composition acting in concert for delivering the drug through an osmotic passageway from the osmotic device.

Yet another object of the invention is to provide an osmotic device having means for high loading of a water insoluble or a slightly water soluble drug and means for delivering the drug in either instance at a controlled rate and continuously over time to a drug recipient.

Yet another object of the invention is to provide an osmotic device that can deliver a pH dependent beneficial agent by providing a neutral medium for delivering the beneficial agent in a finely dispersed form for increasing its surface area and for maximizing the dissolution rate of the beneficial agent.

Still yet another object of the invention is to provide an osmotic system for delivering a drug having a very low dissolution rate that is the rate limiting step for delivering the drug from the system, but now can be delivered by using an osmotic composition that functions in situ as a carrier, as a wetting agent and a solubilizing agent for increasing the dissolution rate and the solubility of the drug, thereby enhancing its delivery from the osmotic system.

Another object of the invention is to provide an osmotic system comprising means for maintaining a high level of osmotic activity of a polymer which polymer is used for delivering a beneficial agent from the osmotic system.

Still a further object of the invention is to provide an osmotic, therapeutic device that can administer a complete pharmaceutical dosage regimen comprising poorly soluble to very soluble agents, at a controlled rate and continuously for a particular time period, the use of which requires intervention only for the initiation and possible termination of the regimen.

Still another object of this invention is to provide an osmotic system manufactured as an osmotic device, which device can house a small amount of a therapeutic agent and dispense small doses of the agent at a controlled rate to the gastrointestinal tract throughout the length of the gastrointestinal tract.

Still another object of the invention is to provide an osmotic system manufactured with a compartment housing a first polymer means and a second polymer means in contacting arrangement that simultaneously maintain their original identity and function as an integrated layer unit for delivering the beneficial drug from the osmotic system.

Still a further object of this invention is to provide an osmotic device that possesses the ability to deliver drugs at a broad range of drug delivery rates, and can deliver the drugs according to a predetermined drug release rate pattern to a biological recipient over time.

Other objects, features, aspects and advantages of the invention will be more apparent to those versed in the dispensing art from the following detailed specification taken in conjunction with the figures and the accompanying claims.

BRIEF DESCRIPTION OF THE DRAWINGS

In the drawings, which are not drawn to scale, but are set forth to illustrate various embodiments of the invention, the drawing figures are as follows:

FIG. 1 is an isometric view of an osmotic device designed for orally administering a beneficial agent to the gastrointestinal tract;

FIG. 2 is an opened view of the osmotic device fo FIG. 1 illustrating the structure of the osmotic device of FIG. 1;

FIG. 3 is an opened view of the osmotic device of FIG. 1 illustrating the osmotic device in operation and delivering a beneficial agent from the osmotic device;

FIG. 4 is an opened view of the osmotic device of FIG. 1 considered with FIG. 3 illustrating the osmotic device in operation and comprising more than one passageway for delivering a major amount of a beneficial agent from the osmotic device;

FIG. 5 shows an osmotic therapeutic device with its wall partially broken away, designed for delivering a beneficial agent into a body passageway, such as the ano-rectal and vaginal passageways;

FIG. 6 shows the osmotic device of FIG. 5 with a different wall structure;

FIG. 7 shows the osmotic device of FIG. 5 depicting a different wall structure than the wall structure depicted in FIG. 6;

In the drawings and the specification, like parts in related figures are identified by reference numerals. The terms appearing earlier in the sepcification and in the description of the drawings, as well as embodiments thereof, are further detailed elsewhere in the disclosure.

DETAILED DESCRIPTION OF THE DRAWINGS

Figure 8:
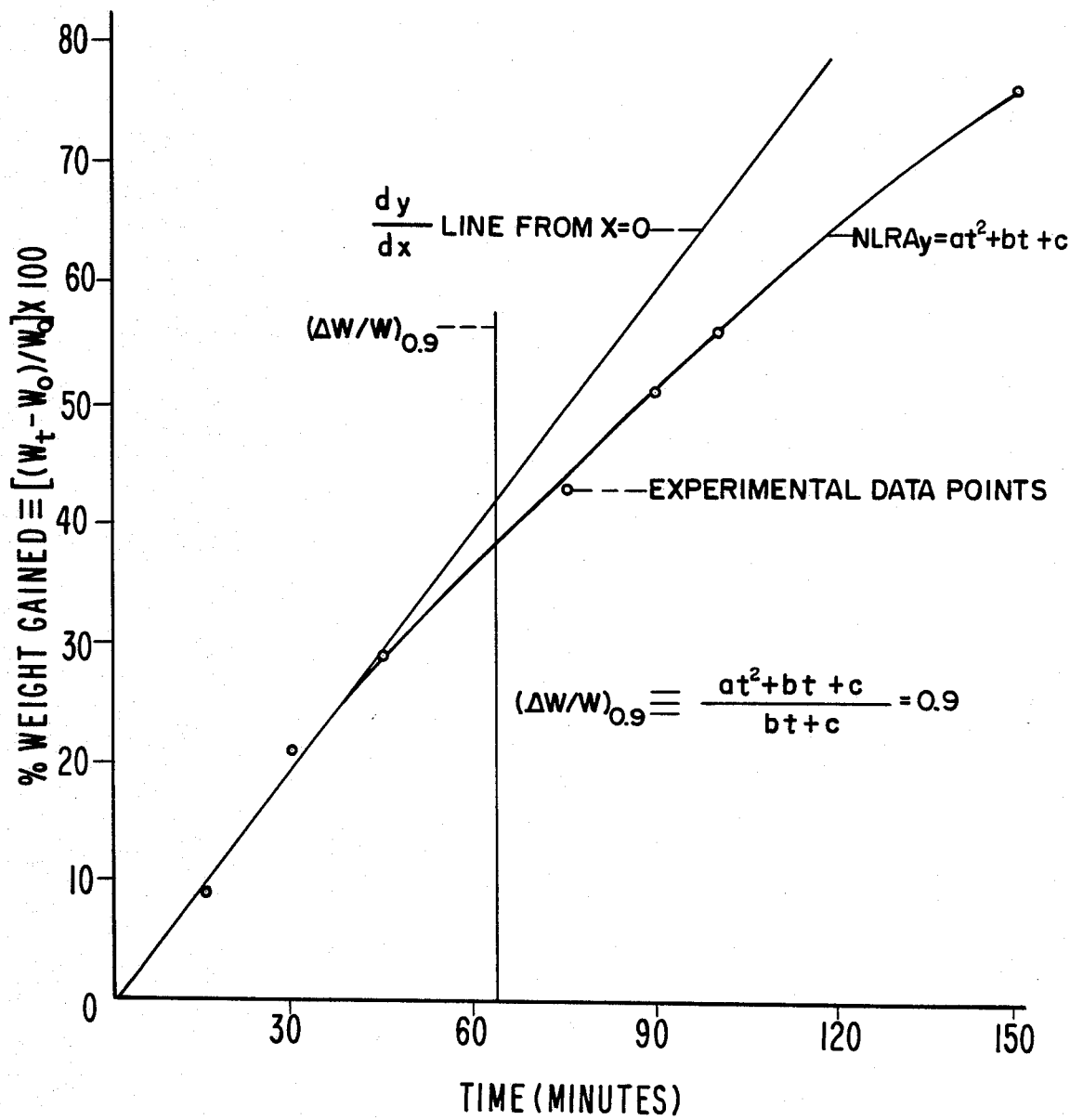
FIG. 8 represents the weight gain as a function of time for a polymer encapsulated in a semipermeable membrane when the encapsulated polymer is placed in water.

Turning now to the drawings in detail, which are examples of various osmotic devices provided by the invention, and which examples are not to be construed as limiting, one example of an osmotic device is seen in FIG. 1. In FIG. 1, osmotic device 10 is seen comprising a body member 11 having a wall 12 and at least one passageway 13 for releasing a beneficial agent from osmotic device 10.

In FIG. 2, osmotic device 10 of FIG. 1 is seen in opened section. In FIG. 2, osmotic device 10 comprises a body 11, a wall 12 that surrounds and forms internal compartment 14, that communicates through a passageway 13 with the exterior of osmotic device 10. Wall 12 is formed totally of a semipermeable composition or in at least a part of a semipermeable composition. When wall 12 comprises in at least a part of a semipermeable composition the remainder of the wall is formed of a non-semipermeable composition. Compartment 14 contains a first osmotic composition comprising a beneficial agent 15, represented by dots, which agent 15 can be from insoluble to very soluble in fluid imbibed into compartment 14, an optional osmagent 16, represented by irregular lines, that is soluble in fluid imbibed into compartment 14 and exhibits an osmotic pressure gradient across semipermeable wall 12 against an external fluid, and an osmopolymer 17, represented by horizontal dashes, that imbibes fluid into compartment 14 and exhibits an osmotic pressure gradient across semipermeable wall 12 against an exterior fluid present in the environment of use. Wall 12 is formed of a semipermeable composition that is substantially permeable to the passage of the exterior fluid, and it is substantially impermeable to the passage of agent 15, osmagent 16 and osmopolymer 17. Semipermeable wall 12 is non-toxic and it maintains its physical and chemical integrity during the delivery life of agent 15 from device 10.

Compartment 14 also houses a second osmotic composition that is distant from passageway 13 and in contacting relation with the first composition. The second composition exerts an expandable driving force that acts in cooperation with the first osmotic composition for delivering the maximum amount of beneficial agent 15 from osmotic device 10. The second osmotic composition comprises an optional osmagent 18, represented by wavy lines, that is soluble in fluid imbibed into compartment 14 and exhibits an osmotic pressure gradient across semipermeable wall 12 against an external fluid, blended in with a presently preferred osmopolymer 19 represented by vertical lines that imbibes fluid into compartment 14 and exhibits an osmotic pressure gradient across semipermeable wall 12 against an external fluid. Osmopolymer 17 and osmopolymer 19 are hydrophilic water soluble or lightly cross-linked water insoluble polymers, and they possess osmotic properties such as the ability to imbibe external fluid through the semipermeable wall, exhibit an osmotic pressure gradient across the semipermeable wall against the external fluid, and swell or expand in the presence of the fluid in the compartment. Osmopolymers 17 and 19 preferably are mixed with osmagent 16 and 18 for imbibing the maximum volume of external fluid into compartment 14. This imbibed fluid is available to osmopolymers 17 and 19 to optimize the volumetric rate and for total expansion of osmopolymer 17 and 19. That is, osmopolymers 17 and 19 absorb fluid imbibed into compartment 14 by the osmotic imbibition action of osmopolymers 17 and 19 supplemented by the osmotic imbibition action of osmagents 16 and 18 for effecting the maximum expansion of osmopolymers 17 and 19 from a rested to an enlarged state.

In operation, the delivery of beneficial agent 15 from osmotic device 10 is carried out, in one presently preferred embodiment, by (1) imbibition of fluid by the first composition to form a fluidic composition in situ and delivery of the suspension through the passageway; and concurrently by (2) imbibition of fluid by the second composition causing the second composition to swell and cooperate with the first composition for driving the agent suspension through the passageway. According to the operation described, the osmotic device may be considered as a cylinder, with the second composition expanding like the movement of a piston for aiding in delivering the agent composition from the osmotic device.

The operation of a dispenser 10 manufactured according to the invention is set forth in this example. The volume imbibition rate of the push formulation in compartment 14 is equal to the volume rate of water imbibition $(dV/dt)_p$ by the osmotic agent formulation (17, 19, 16, 18) expressed by equation (1) as follows:

$$\frac{dV}{dt}\bigg|_p = \frac{k}{h} A_p \cdot \Delta\pi \tag{1}$$

where k is the water permeability of the semipermeable wall, h is the thickness of the wall, $A_p$ is the wall surface of the push compartment exposed to the osmotic process, and $\Delta\pi$ is the osmotic pressure difference of the push formulation across the wall. The geometrical shape considered here is as shown in FIG. 2, with flat bottom and cylindrical body. The volume rate of water imbibition can be related to the total surface area for water transport A from the end and cylindrical sections from equations (2) and (3):

$$A_p = r^2 + 2\pi r l \tag{2}$$

where l is the height of the osmotic formulation.

$$A_p = \pi r^2 + \frac{2}{r} V \tag{3}$$

where V is the volume of osmotic formulation. The volume of the osmotic driving member equals equation (4a) and the volume expansion is given by equation (4b):

$$V = V_o + V_H \tag{4a}$$

$$V - V_o = V_H \tag{4b}$$

where $V_o$ and $V_H$ are, respectively, the volumes of dry osmotic agent formulation and water imbibed. Alternatively, equation (4a) can be written:

$$V = \frac{W_o}{\rho_o} + \frac{W_H}{\rho_H} \tag{5}$$

where $\rho_o$ is the density of dry osmotic agent formulation, $W_o$ and $W_H$ are the weights of osmotic agent and water imbibed, and $\rho_H$ is the density of water.

Rearranging terms within the equations, the following equation (6) results:

$$V = \frac{W_o}{\rho_o}\left(1 + \frac{W_H}{W_o} \cdot \frac{\rho_o}{\rho_H}\right) \tag{6}$$

and $$A_p = \pi r^2 + \frac{2}{r} \frac{W_o}{\rho_o}\left(1 + \frac{W_H}{W_o} \cdot \frac{\rho_o}{\rho_H}\right) \tag{7}$$

Therefore, the volume rate of water imbibition is expressed by:

$$\frac{dV}{dt}\bigg)_p = \frac{k}{h}\left\{\pi r^2 + \frac{2}{r}\left(1 + \frac{\rho_o}{\rho_H}\frac{W_H}{W_o}\right)\frac{W_o}{\rho_o}\right\}\Delta\pi \qquad (8)$$

The release rate of the drug from dispenser can be written as shown in equation (9) where F and Q are, respectively, the volume flow into the drug and osmotic push compartment.

$$\frac{dm}{dt} = (F + Q)C_d \qquad (9)$$

Here $C_d$ is the concentration of drug in the dispensed formulation.

Equation (9) considered in conjunction with equation (8), allows for numerous delivery rates and drug programs based on different shapes of device 10 and the osmotic pressure in the dispenser as a function of time.

For development of the example, equation (10) will be substituted in the subsequent equations.

$$H = \frac{W_H}{W_o} \qquad (10)$$

The composition of the driving push composition is formulated with osmotically active polymer compositions which exhibit an osmotic pressure as a function of hydration as shown for membranes of two pumping rates. The osmotic pressure can be described by equation (11) and equation (12).

$$\Delta\pi = C \cdot \exp(-NH) \qquad (11)$$

$$\Delta\pi = \Delta\pi(H) \qquad (12)$$

where C and N are constants characterized by the formulation and the nature of the osmotic agent.

Substituting equation (12) and equation (13) in equation (1), equation (14) results as follows:

$$A_p(H) = \pi r^2 + \frac{2}{r}\left(1 + \frac{\rho_o}{\rho_H}H\right)\frac{W_o}{\rho_o} \qquad (13)$$

$$\left(\frac{dV}{dt}\right)_p = \frac{k}{h} \cdot A_p(H) \cdot \Delta\pi(H) \qquad (14)$$

In addition, equation (15) holds for the volume of absorbed water $V_H$ $$V_H = \frac{W_H}{\rho_H} = H \cdot \frac{W_o}{\rho_H} \qquad (15)$$

Since the volume of formulation displaced equation (16) is related to H by equation (15), $$\left(\frac{dV}{dt}\right)_p = \frac{dV_H}{dt} \qquad (16)$$

it follows that equation (17) results:

$$\frac{dH}{dt} = \frac{\rho_H}{W_o} \cdot \frac{k}{h} \cdot A_p(H) \cdot \Delta\pi(H) = f(H) \qquad (17)$$

The solution of this differential equation will result in H(t) which can be substituted in equation (14) to yield the release rate. The solution to equation (17) was solved by numerical integration, resulting in the simulations for the release rates given in FIG. 14. The numerical integration of equation (17) is obtained from equation (18) as follows:

$$\int_0^H \frac{dH}{f(H)} = \int_0^t dt \qquad (18)$$

The final value at shutdown for device 10 for $H_f$ and $t_f$ is given by equation (19):

$$H_f = \frac{\rho_H}{\rho_{dc}} \cdot \frac{W_{dc}}{W_o} \qquad (19)$$

Here $\rho_{dc}$ and $W_{dc}$ are the density and weight of the drug compartment 14. The function H(t) is obtained by finding the time $t_i$ associated with the hydration value $H_i$. The final value of H, $H_f$ equation (19), can be reached after m equal steps $\Delta H$, such that equation (20) results, and also equation (21).

$$\Delta H_j = \frac{H_f}{m} \qquad (20)$$

$$H_i(t_i) = \sum_{j=1}^{i} \Delta H_j \qquad (21)$$

The time $t_i$ associated with $H_i$ is calculated from equation (22) where $\overline{f(H_j)}$ is the average value of expression (17) between the start and end of the interval i:

$$t_i = \sum_{j=1}^{i} \Delta t_j \qquad (22)$$

Here $\Delta t_j$ is given by equation (23):

$$t_j = \frac{\Delta H_i}{\overline{f(H)}_j} \qquad (23)$$

From equations (15), (16) and (23), it follows then that the volume push rate $(dV/dt)_p(t)$ as a function of time is given by equation (24):

$$\left(\frac{\Delta V}{\Delta t}\right)_p(t) = \frac{W_o}{\rho_H} \cdot \left(\frac{\Delta H_i}{\Delta t_i}\right) \qquad (24)$$

The concentration $C_d$ of drug in the dispensed formulation can be written as shown in equation (25):

$$C_d = C_o \cdot F_D \qquad (25)$$

where $C_o$ is the concentration of solids dispensed and $F_D$ the fraction of drug in the dispensed formulation. This fraction of drug $F_D$ can be assumed to be equal to the fraction of drug formulated in the compartment in the dry state if the drug formulation is dispensed uniformly.

These push-pull systems operate favorably in a region where the drug compartment formulates drug in suspension at a constant rate and wherein the push compartment dispenses this formulation at a constant rate. Such condition is achieved when the majority of semisolid drug formulation is dispensed such that the total drug delivery rate can be expressed by equation (26):

$$\frac{dm}{dt} = \left(\frac{dV}{dt}\right)_p F_D \cdot \rho_{dc} \qquad (26)$$

The influx of water in the drug compartment $F=(dV/dt)_D$ is responsible for converting the solid drug formulation into a fluid form of concentration $C_d$. The volume flux F adds to the osmotic driving flux $Q=(dV/dt)_p$ to yield equation (27):

$$\frac{dm}{dt} = (Q + F) \cdot C_D \qquad (27)$$

By equating equation (9) and equation (27) and considering equation (25) the concentration of dispensed solids $C_o$ can be found to be given by equation (28); also $C_o$ can be verified independently.

$$C_o = \frac{Q \cdot \rho_{dc}}{F + Q} \qquad (28)$$

Based on the above description three push-pull osmotic systems were designed to deliver doxazosin with parameters as listed in Table 1. The density of the push and drug composition was respectively 1.3 and 1.1 gr/ml.

TABLE 1

| | | | |
|---|---|---|---|
| Diameter (cm) | 0.89 | 0.89 | 1.13 |
| Drug content (mg) (as base) | 2.2 | 4.4 | 8.8 |
| Fraction of drug in dry compartment $F_D$ | 0.0147 | 0.0293 | 0.0293 |
| Weight of drug layer (mg) | 150 | 150 | 300 |
| Weight of push layer (mg) | 100 | 100 | 200 |
| Membrane thickness (cm) | $9.9 \times 10^{-3}$ | $10.4 \times 10^{-3}$ | $11.0 \times 10^{-3}$ |
| Thickness, h(mil) | 3.9 | 4.1 | 4.7 |
| Membrane permeability (K) | $9.4 \times 10^{-7}$ | $9.4 \times 10^{-7}$ | $9.4 \times 10^{-7}$ |
| Total system area A(cm$^2$) | 2.25 | 2.25 | 3.44 |

FIGS. 3 and 4 illustrate the osmotic device in operation as described for FIGS. 1 and 2. In FIGS. 3 and 4, for osmotic device 10, fluid is imbibed by the first composition at a rate determined by the permeability of the wall and the osmotic pressure gradient across the wall. The imbibed fluid continuously forms a solution containing beneficial agent, or a suspension, or a gel comprising an optional osmagent and osmopolymer containing beneficial agent in suspension, which solution or suspension in either operation is released by the combined operations of device 10. These operations include the solution, or the suspension being osmotically delivered through the passageway due to the continuous formation of solution or suspension, and by the swelling and increasing volume of the different second composition, represented by the increase in height of the vertical lines in FIGS. 3 and 4. This latter swelling and increase in volume applies pressure against the solution or suspension thereby aiding the first composition and simultaneously causing delivery of beneficial agent through the osmotic passageway 13, which can have more than one passageway as seen in FIG. 4 comprising, for example, a microporous insert, or pores formed by leaching a leachable or fluid removable material thereby providing pore-passageways for releasing drug to the exterior of the device. Thus, the osmotic device provided by this invention can be viewed as a single unit construction device comprising two compositions containing two polymeric structures acting in concert for effective drug administration to a patient.

The first composition and the second composition act together to substantially insure that delivery of beneficial agent from the compartment is controlled and constant over a prolonged period of time by two methods. First, the first composition imbibes external fluid across the wall, thereby forming either a solution or a suspension, which is substantially delivered at non-zero order, without the second composition present, since the driving force decays with time. Second, the second composition operates by imbibing external fluid across the wall continuously and, consequently, increases in volume thereby exerting a force against the first composition and diminishing the volume of beneficial agent first composition. Thus, the expansion of the second compartment can be made very zero order which directs beneficial agent formulation to the passageway in the compartment. Additionally, as the composition formed in the first composition is squeezed out, that is, delivered from device 10, the remaining osmotic composition closely contacts the internal wall and generates a constant osmotic pressure and, therefore, a constant delivery rate in conjunction with the second composition. The swelling and expansion of the second composition, with its accompanying increase in volume, along with the simultaneous corresponding reduction in volume of the first composition assures the delivery of beneficial agent through the osmotic passageway at a controlled rate over time.

Device 10 of FIGS. 1 through 4 can be made into many embodiments including the presently preferred embodiments for oral use; for releasing either a locally or systemically acting therapeutic agent in a gastrointestinal tract. Oral system 10 can have various conventional shapes and sizes such as round with a diameter of 3/16 inches to ⅜ inches. In these forms system 10 can be adapted for administering beneficial agent to numerous animals, including warm blooded animals, humans, avians, reptiles and pisces.

FIGS. 5, 6 and 7 show another embodiment provided by this invention. FIGS. 5, 6 and 7 show an osmotic device 10 designed for placement in a body passageway, such as a vagina, or the ano-rectal canal. Device 10 has an elongated, cylindrical, self-sustaining shape with a curved lead end 20, a trailing end 21, and it is equipped with manually controlled strings 22 for easily removing device 10 from the biological passageway. Device 10 is structurally identical with the device described above in FIGS. 1 through 4, and it operates in a like manner. In FIG. 5, device 10 is depicted with a semipermeable wall 23, in FIG. 6 with a laminated wall 24 comprising an inner semipermeable lamina 25 adjacent to compartment 14 and an external microporous lamina 26 distant from compartment 14. The micropores of which wall can serve as a pore-passageway drug releasing means. In FIG. 7, device 10 comprises a laminated wall 28 formed of a microporous lamina 29 next to compartment 14, and a semipermeable lamina 30 facing the environment of use and in laminar arrangement with microporous lamina 29. The semipermeable lamina used for manufacturing these osmotic devices is permselective since it is permeable to the passage of fluid and substantially impermeable to the passage of agent, osmagent and osmopolymer. The micropores in lamina 29 can align with the passageway of lamina 30 for releasing drug from device 10. Device 10 delivers a beneficial agent for absorption by the vaginal mucosa, or the anorectal mucosa, to produce an in vivo local or systemic effect over a prolonged period of time.

The osmotic devices of FIGS. 1 through 7 can be used for delivering numerous agents including drugs at a controlled rate independent of the drug pH dependency, or where the dissolution rate of the agent can vary between low and high in fluid environments, such as gastric fluid and intestinal fluid. The osmotic devices also provide for the high loading of agents of low solubility and their delivery at meaningful, therapeutic amounts. While FIGS. 1 through 7 are illustrative of various osmotic devices that can be made according to the invention, it is to be understood these devices are not to be construed as limiting, as the devices can take a wide variety of shapes, sizes and forms adapted for delivering beneficial agents to the environment of use. For example, the devices include buccal, implant, artificial gland, cervical, intrauterine, ear, nose, dermal, subcutaneous, and like delivery devices. The devices also can be sized, shaped, structured and adapted for delivering an active agent in streams, aquariums, fields, factories, reservoirs, laboratory facilities, hot houses, transportation means, naval means, military means, hospitals, veterinary clinics, nursing homes, farms, zoos, sickrooms, chemical reactions, and other environments of use.

DETAILED DESCRIPTION OF THE INVENTION

In accordance with the practice of this invention it has now been found that osmotic delivery device 10 can be manufactured with a first osmotic composition and a different second osmotic composition mutually housed in cooperative relationship in the compartment of the device. The compartment is formed by a wall comprising a material that does not adversely affect the beneficial agent, osmagent, osmopolymer, and the like. The wall is semipermeable, that is the wall is permeable to the passage of an external fluid such as water and biological fluids, and it is substantially impermeable to the passage of agents, osmagents, osmopolymers, and the like. The wall comprises a material that does not adversely affect an animal, or host, or the components comprising the device, and the selectively semipermeable materials used for forming the wall are non-erodible and they are insoluble in fluids. Typical materials for forming the wall are in one embodiment cellulose esters, cellulose ethers and cellulose ester-ethers. These cellulosic polymers have a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, mono-, di- and tricellulose alkanylates; mono-, di- and tricellulose aroylates, and the like. Exemplary polymers include cellulose acetate having a D.S. up to 1 and an acetyl content up to 21%; cellulose acetate having an acetyl content of 32 to 39.8%; cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers include cellulose propionate having a D.S. of 1.8 and a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, co-esters of cellulose such as cellulose acetate butyrate and cellulose acetate propionate, and the like.

Additional semipermeable polymers include acetaldehyde dimethyl cellulose acetate, cellulose acetate ethyl carbamate, cellulose acetate methyl carbamate, cellulose acetate dimethyl aminoacetate, semipermeable polyamides; semipermeable polyurethanes; semipermeable sulfonated polystyrenes; semipermeable cross-linked selectively permeable polymers formed by the coprecipitation of a polyanion and a polycation as disclosed in U.S. Pat. Nos. 3,173,876; 3,276,586; 3,541,005; 3,541,006, and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); semipermeable cross-linked poly(vinylbenzyltrimethyl ammonium chloride); semipermeable polymers exhibiting a fluid permeability of $2.5 \times 10^{-8}$ to $2.5 \times 10^{-4}$ ($cm^3$-cm/$cm^2$ hr atm) expressed per atmosphere of hydrostatic or osmotic pressure difference across the semipermeable wall. The polymers are known to the art in U.S. Pat. Nos. 3,845,770; 3,916,899; and 4,160,020; and in *Handbook of Common Polymers* by Scott, J. R. and Roff, W. J., (1971), published by CRC Press, Cleveland, Ohio.

The laminated wall comprising a semipermeable lamina and a microporous lamina are in laminar arrangement and they act in concert to form an integral laminated wall that maintains its physical and chemical integrity and does not separate into the original lamina throughout the operative agent release history of the osmotic device. The semipermeable lamina is made from the semipermeable polymeric materials, the semipermeable homopolymers, and the semipermeable copolymers presented above, and the like.

Microporous lamina suitable for manufacturing the laminated osmotic device generally comprise preformed microporous polymeric materials, and polymeric materials that can form a microporous lamina in the environment of use. The microporous materials in both embodiments are laminated to form the laminated wall. The preformed materials suitable for forming the microporous lamina are essentially inert, they maintain their physical and chemical integrity during the period of agent release and they can be described generically as having a sponge like appearance that provides a supporting structure for a semipermeable lamina and also provides a supporting structure for microscopic sized interconnected pores or voids. The microporous materials can be isotropic wherein the structure is homogeneous throughout a cross sectional area, or they can be anisotropic wherein the structure is non-homogeneous throughout a cross sectional area. The pores can be continuous pores that have an opening on both faces of a microporous lamina, pores interconnected through tortuous paths of regular and irregular shapes, including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and the number of pores. The pore size of a microporous lamina is easily ascertained by measuring the observed pore diameter at the surface of the material under the electron microscope. Generally, materials possessing from 5% to 95% pores and having a pore size of from 10 angstroms to 100 microns can be used for making a microporous lamina.

The pore size and other parameters characterizing the microporous structure also can be obtained from flow measurements, where a liquid flux, J, is produced by a pressure difference P, across the lamina. The liquid flux through a lamina with pores of uniform radius extended through the lamina and perpendicular to its surface with area A given by equation (29):

$$J = \frac{N \pi r^2 \Delta P}{8\eta \Delta x} \quad (29)$$

wherein J is the volume transported per unit time and lamina area containing N number of pores of radius r, $\eta$ is the viscosity of the liquid and $\Delta P$ is the pressure difference across the lamina with thickness $\Delta x$. For this type of lamina, the number of pores N can be calculated from relation (30), wherein $\epsilon$ is the porosity defined as the ratio of void volume to total volume of the lamina; and A is the cross sectional area of the lamina containing N pores.

$$N = \frac{\epsilon A}{\pi r^2} \quad (30)$$

The pore radius then is calculated from equation (31):

$$r = \left[ 8\eta \frac{\Delta x \tau}{\Delta p \epsilon} J' \right]^{\frac{1}{2}} \quad (31)$$

wherein J' is the volume flux through the lamina per unit area produced by the pressure difference $\Delta P$ across the lamina, $\eta$, and $\Delta x$ having the meaning defined above and $\tau$ is the tortuosity defined as the ratio of the diffusional path length in the lamina to the lamina thickness. Relations of the above type are discussed in *Transport Phenomena In Membranes*, by Lakshminatayanaiah, N. Chapter 6, (1969), published by Academic Press, Inc., New York.

As discussed in this reference, supra, on page 336, in Table 6.13, the controlled porosity of the lamina having pores with radius r can be expressed relative to the size of the transported molecule having a radius a, and as the ratio of molecular radius to pore radius a/r decreases, the lamina becomes porous with respect to this molecule. That is, when the ratio a/r is less than 0.3, the lamina becomes substantially microporous as expressed by the osmotic reflection coefficient which decreases below 0.5. Microporous lamina with a reflection coefficient in the range of less than 1, usually from 0 to 0.5, and preferably less than 0.1 with respect to the active agent are suitable for fabricating the system. The reflection coefficient is determined by shaping the material in the form of a lamina and carrying out water flux measurements as a function of hydrostatic pressure difference and as a function of the osmotic pressure difference caused by the active agent. The osmotic pressure difference creates a hydrostatic volume flux, and the reflection coefficient is expressed by equation (32):

$$\sigma = \frac{\text{osmotic volume flux}}{\text{hydrostatic volume flux}} \quad (32)$$

Properties of microporous materials are described in *Science*, Vol. 170, pp 1302-1305, (1970); *Nature*, Vol. 214, page 285, (1967); Polymer *Engineering and Science*, Vol. 11, pp 284-288, (1971); U.S. Pat. Nos. 3,567,809 and 3,751,536; and in *Industrial Processing With Membranes*, by Lacey, R. E., and Loeb, Sidney, pp 131-134, (1972).

Microporous materials having a preformed structure are commercially available and they can be made by art known methods. The microporous materials can be made by etching, nuclear tracking, by cooling a solution of flowable polymer below the freezing point whereby solvent evaporates from the solution in the form of crystals dispersed in the polymer and then curing the polymer followed by removing the solvent crystals, by cold or hot stretching at low or high temperatures until pores are formed, by leaching from a polymer a soluble component by an appropriate solvent, by ion exchange reaction, and by polyelectrolyte process. Process for repairing microporous materials are described in *Synthetic Polymer Membranes*, by R. E. Kesting, (1971), Chapters 4 and 5, published by McGraw Hill, Inc., *Chemical Reviews*, "Ultrafiltration", Vol. 18, pp 373 to 455, (1934); *Polymer Eng. and Sci.*, Vol. 11, No. 4, pp 284-288, (1971), *J. Appl. Poly. Sci.*, (1971), Vol. 15, pp 811-829, (1971); and in U.S. Pat. Nos. 3,565,259; 3,615,024; 3,751,536; 3,801,692; 3,852,224, and 3,849,528.

Microporous materials useful for making the lamina include microporous polycarbonates comprised of linear polyesters of carbonic acid in which carbonate groups recur in the polymer chain; microporous materials prepared by the phosgenation of a dihydroxyl aromatic, such as bisphenol A; microporous poly(vinyl chloride); microporous polyamides such as polyhexamethylene adipamide; microporous modacrylic copolymers including those formed from 60% vinyl chloride and 40% acrylonitrile; styrene acrylic copolymers; porous polysulfones characterized by diphenylene sulfone groups in a linear chain thereof; poly(vinylidene) halides; polychloroethers; acetal polymers; polyesters prepared by esterification of a dicarboxylic acid or anhydride with an alkylene polyol; poly(alkylenesulfides); phenolic polyesters; microporous poly(saccharides); having substituted and unsubstituted anhydroglucose units exhibiting a higher permeability to the passage of water and biological fluids than a semipermeable lamina; asymmetric porous polymers; cross-linked olefin polymers; hydrophobic or hydrophilic microporous homopolymers, copolymers or interpolymers having a reduced bulk density; and materials described in U.S. Pat. Nos. 3,597,752; 3,643,178; 3,654,066; 3,709,774; 3,718,532; 3,803,061; 3,852,224; 3,853,601; and 3,852,388, in British Pat. No. 1,126,849, and in *Chem. Abst.*, Vol. 71, 4274F, 22572F, 22573F, (1969).

Additional microporous materials include microporous poly(urethanes); microporous cross-linked, chain extended poly(urethanes); microporous poly(urethanes) in U.S. Pat. No. 3,524,753; microporous poly(imides); microporous poly(benzimidazoles); regenerated microporous proteins; semi-solid, cross-linked microporous poly(vinylpyrrolidone); microporous materials prepared by diffusion of multivalent cations into polyelectrolyte sols as in U.S. Pat. No. 3,565,259; anisotropic microporous materials of ionically associated polyelectrolytes; porous polymers formed by the coprecipitation of a polycation and a polyanion as described in U.S. Pat. Nos. 3,276,589; 3,541,055; 3,541,066 and 3,546,142; derivatives of poly(styrene), such as microporous poly(sodium styrenesulfonate) and microporous poly(vinyl benzyltrimethyl ammonium chloride), the microporous materials disclosed in U.S. Pat. No. 3,615,024, U.S. Pat. Nos. 3,646,178, 3,852,224, and the like.

Further, the micropore forming material used for the purpose of the invention includes the embodiment wherein the microporous lamina is formed in situ by a pore former being removed by dissolving, or extracting, or leaching it to form the microporous lamina during the operation of the system. The pore former can be a solid or a liquid. The term, "liquid," for this invention, embraces semi-solids and viscous fluids. The pore formers can be inorganic or organic. The pore formers suitable for the invention include pore formers that can be extracted or removed without any chemical change in the polymer. The pore forming solids have a size of about 0.1 to 200 micrometers and they include alkali metal salts such as sodium chloride, sodium bromide, potassium chloride, potassium sulfate, potassium phosphate, sodium benzoate, sodium acetate, sodium citrate, potassium nitrate, and the like. The alkali earth metal salts include calcium phosphate, calcium nitrate, and the like. The transition metal salts include ferric chloride, ferrous sulfate, zinc sulfate, cupric chloride, manganese fluoride, manganese fluorosilicate, and the like. The pore formers include organic compounds such as polysaccharides. The polysaccharides include the sugars: sucrose, glucose, fructose, mannose, galactose, aldohexose, altrose, talose, lactose, monosaccharides and disaccharides; and polyalcohols such as mannitol and sorbitol. Also, organic aliphatic and aromatic oils and solids, including diols and polyols, as exemplified by polyhydric alcohols, poly(alkylene glycols), polyglycols, alkylene glycols, poly(alpha-omega)-alkylenediols esters or alkylene glycols and the like; water soluble cellulosic polymers such as hydroxyloweralkyl cellulose, hydroxypropyl methylcellulose, methyl cellulose, methylethyl cellulose, hydroxyethyl cellulose and the like; water soluble polymers such as polyvinylpyrrolidone, sodium carboxymethylcellulose and the like. The pore formers on their removal from the lamina form channels through the lamina. In a preferred embodiment the non-toxic, pore forming agents are selected from the group consisting of inorganic and organic salts, carbohydrates, polyalkylene glycols and water soluble polymers used for forming a microporous lamina in a biological environment. Generally, for the purpose of this invention, when the polymer forming the microporous lamina contains more than 15% by weight of a pore former, the polymer is a precursor microporous lamina that on removing the pore former yields a lamina which is substantially microporous.

The expression, "passageway," as used herein, comprises means and methods suitable for releasing the agent or drug from the osmotic system. The expression includes osmotic aperture, osmotic orifice, osmotic hole or osmotic bore through the semipermeable wall or the laminated wall. The osmotic passageway can be formed by mechanical drilling, laser drilling or by eroding an erodible element such as a gelatin plug in the environment of use, or formed in situ by leaching of a material or by cracking of the wall. A detailed description of osmotic passageways, and the maximum and minimum dimensions for a passageway, are disclosed in U.S. Pat. Nos. 3,845,770 and 3,916,899. The osmotically calibrated passageway has a maximum cross-sectional area, $A_s$, defined by the equation (33) as follows:

$$A_{s\ (max)} = \frac{L}{F} \times \frac{Q_p}{t} \times \frac{1}{DS} \tag{33}$$

wherein L is the length of the passageway $Q_p/t$ is the mass delivery rate of the agent, D is the diffusion coefficient of the agent, S is the solubility of the agent in the fluid, and F is from 2 to 1000, said passageway having a minimum area $A_s$ defined by equation (34) as follows:

$$A_{s\ (min)} = \left[\frac{Lv}{t} \times 8 \times \frac{\pi\eta}{P}\right]^{\frac{1}{2}} \tag{34}$$

wherein L is the length of the passageway, v/t is the agent solution volume delivery rate, $\pi$ is 3.14; $\eta$ is the viscosity of agent solution dispensed from the device and $\Delta P$ is the hydrostatic pressure difference between the inside and the outside of the compartment having a value up to 20 atmospheres.

The passageway for releasing drug can comprise one passageway, or more than one passageway. As disclosed in U.S. Pat. No. 3,916,899 the term, "passageway," includes operating equivalents such as aperture, orifice, bore, porous element, hollow fiber, capillary tube, erodible material and the like. The passageway can also be a pore as disclosed in U.S. Pat. No. 4,200,098 comprising a pore-passageway formed by leaching a leachable such as sorbitol from a cellulose acetate wall. The pores are provided for the effective release of a beneficial agent such as a drug to the exterior of the osmotic device. Pores formed in the wall of an osmotic device, formed by dissolving, leaching or extracting a pore former such as sorbitol, lactose, or the like, from a cellulose acylate wall to form a pore of controlled size or controlled porosity for the effective release of a beneficial drug from an osmotic core of an osmotic device are known to the prior art in U.S. Pat. No. 4,285,987.

The osmotically effective compounds that can be used for the purpose of this invention include inorganic and organic compounds that exhibit an osmotic pressure gradient across the semipermeable wall, or across a semipermeable microporous laminated wall, against an external fluid. The osmotically effective compounds, along with the osmopolymers, imbibe fluid into the osmotic device thereby making available in situ fluid for imbibition by an osmopolymer to enhance its expansion, and/or for forming a solution or suspension containing a beneficial agent for its delivery through a passageway from the osmotic device. The osmotically effective compounds are known also as osmotically effective solutes, or osmagents.

The osmotically effective compounds are used by mixing them with a beneficial agent and osmopolymer for forming a solution, or suspension containing the beneficial agent that is osmotically delivered from the device. The expression limited solubility as used herein means the agent has a solubility of about less than 5% by weight in the aqueous fluid present in the environment. The osmotic solutes are used by homogeneously or heterogeneously mixing the solute with the agent or osmopolymer and then charging them into the reservoir, for example, the solutes and osmopolymers attract fluid into the reservoir producing a solution or a suspension of solute in a gel which is delivered from the system concomitantly transporting undissolved and dissolved beneficial agent to the exterior of the system. Osmotically effective solutes used for the former purpose include magnesium sulfate, magnesium chloride, potassium sulfate, sodium sulfate, lithium sulfate, potassium acid phosphate, d-mannitol, urea, inositol, magnesium succinate, tartaric acid, carbohydrates such as raffinose, sucrose, glucose, alpha-d-lactose monohydrate, and mixtures thereof. The amount of osmagent in the compartment will generally be from 0.01% to 30% or higher in the first composition, and usually from 0.01% to 40% or higher in the second composition.

The osmotic solute is initially present in excess and it can be in any physical form that is compatible with the beneficial agent, the osmagent, and the osmopolymer. The osmotic pressure of saturated solutions of various osmotically effective compounds and for mixtures of compounds at 37° C., in water, is listed in Table 1. In the table, the osmotic pressure pi, is in atmospheres, atm. The osmotic pressure is measured in a commercially available osmometer that measures the vapor pressure difference between pure water and the solution to be analyzed and, according to standard thermodynamic principles, the vapor pressure ratio is converted into osmotic pressure difference. In Table 1, osmotic pressures of from 20 atm to 500 atm are set forth. Of course, the invention includes the use of lower osmotic pressures from zero, and higher osmotic pressures than those set forth by way of example in Table 1. The osmometer used for the present measurements is identified as Model 320B, Vapor Pressure Osmometer, manufactured by the Hewlett Packard Co., Avondale, Pa.

TABLE 2

| COMPOUND OR MIXTURE | OSMOTIC PRESSURE ATM |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Manitol-Sucrose | 170 |
| Dextrose | 82 |
| Potassium Sulfate | 39 |
| Mannitol | 38 |
| Sodium Phosphate Tribasic 12 $H_2O$ | 36 |
| Sodium Phosphate Dibasic 7 $H_2O$ | 31 |
| Sodium Phosphate Dibasic 12$H_2O$ | 31 |
| Sodium Phosphate Dibasic Anhydrous | 29 |
| Sodium Phosphate Monobasic $H_2O$ | 28 |

The osmopolymers suitable for forming the first osmotic composition, and also suitable for forming the second osmotic composition, are osmopolymers that exhibit fluid imbibition properties. The osmopolymers are swellable, hydrophilic polymers which osmopolymers interact with water and aqueous biological fluids and swell or expand to an equilibrium state. The osmopolymers exhibit the ability to swell in water and retain a significant portion of the imbibed water within the polymer structure. The osmopolymers swell or expand to a very high degree, usually exhibiting a 2 to 50 fold volume increase. The osmopolymers can be noncross-linked or cross-linked. The swellable, hydrophilic polymers are in one presently preferred embodiment lightly cross-linked, such cross-links being formed by covalent or ionic bonds. The osmopolymers can be of plant, animal or synthetic origin. The osmopolymers are hydrophilic polymers. Hydrophilic polymers suitable for the present purpose include poly(hydroxy alkyl methacrylate) having a molecular weight of from 30,000 to 5,000,000; poly(vinylpyrrolidone) having molecular weight of from 10,000 to 7,500,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose, cross-linked agar and carboxymethyl cellulose; a water insoluble, water swellable copolymer produced by forming a dispersion of finely divided copolymer or maleic anhydride with styrene, ethylene, propylene, butylene or isobutylene cross-linked with from 0.001 to about 0.5 moles of saturated cross-linking agent per mole of maleic anhydride in copolymer; water swellable polymers of N-vinyl lactams, and the like.

Other osmopolymers include polymers that form hydrogels such as Carbopol ® acidic carboxy polymers having a molecular weight of 450,000 to 4,000,000; Cyanamer ® polyacrylamides; cross-linked water swellable indene-maleic anhydride polymers, Goodrite ® polyacrylic acid having a molecular weight of 80,000 to 200,000; Polyox ® polyethylene oxide polymers having a molecular weight of 100,000 to 5,000,000 and higher; starch graft copolymers; Aqua-Keeps ® acrylate polymer polysaccharides composed of condensed glucose units such as diester cross-linked polyglucan, and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels; and in *Handbook of Common Polymers,* by Scott and Roff, published by the Chemical Rubber Company, Cleveland, Ohio. The amount of osmopolymer in the first osmotic composition is about 0.01 to 90%, and the amount of osmopolymer in the second osmotic composition is 15 to 95%, with the total weight of all ingredients in a composition equal to 100%. In a presently preferred embodiment, the osmopolymer identified as P1 comprising the first composition is different than the osmopolymer identified as P2 comprising the second composition. The osmopolymer in the first composition can be structurally different than the osmopolymer in the second composition. Or, the osmopolymers can be substantially structurally identical with proviso the molecular weight of the osmopolymer in the second osmotic composition is larger than the molecular weight of the osmopolymer in the first composition. The osmopolymer P1 comprising the first composition serves as a pharmaceutically acceptable carrier for the active agent and it also contributes to the driving force that cooperates with osmopolymer P2 comprising the second composition that delivers the agent through the passageway from the device. During operation of the device fluid is imbibed into the device resulting in the viscosity of P2 being greater than the viscosity of P1. In this operation P1 and P2 operate as a single unit substantially free of a void between their interfaced contacting surfaces of osmopolymer P1 and P2 for successful delivery of the beneficial agent from the osmotic device.

Osmopolymer fluid imbibition determination for a chosen polymer can be made by following the procedure described below. A round dye having an inner diameter of ½ inch, fitted with a ½ inch diameter stainless steel plug, is charged with a known quantity of polymer with the plugs extending out either end. The plugs and the die were placed in a Carver press with plates between 200° F. and 300° F. A pressure of 10,000 to 15,000 psi was applied to the plugs. After 10 to 20 minutes of heat and pressure the electrical heating to the plates was turned off, and tap water circulated through the plates. The resulting ½ inch disks were placed in an air suspension coater charged with 1.8 kg saccharide cores, placebo cores, made of any sugar such as lactose, and so forth, and coated with cellulose acetate having an acetyl content of 39.8% dissolved in 94:6 w/w, $CH_2Cl_2/CH_3OH$, to yield a 3% w/w solution. The coated systems were dried overnight at 50° C. The coated disks were immersed in water at 37° C. and periodically removed for a gravimetric determination of water imbibed. The initial imbibition pressure was calculated by using the water transmission constant for the cellulose acetate, after normalizing imbibition values for membrane surface area and thickness. The polymer used in this determination was the sodium derivative of Carbopol-934 ® polymer, prepared according to the procedure of B. F. Goodrich Service Bulletin GC-36, "Carbopol ® Water-Soluble Resins", page 5, published by B. F. Goodrich, Akron, OH.

The cumulative weight gain values, y, as a function of time, t, for the water soluble polymer disk coated with the cellulose acetate were used to determine the equation of the line $y = c + bt + at^2$ passing through those points by a least square fitting technique.

The weight gain for the Na Carbopol-934 ® is given by the equation (35) that follows: Weight gain equals $0.359 + 0.665t - 0.00106t^2$ wherein t is elapsed time in minutes. The rate of water flux at any time will be equal to the slope of the line that is given by the following equations (35) and (36).

$$\frac{dy}{dt} = \frac{d(0.359 + 0.665t - 0.00106t^2)}{dt} \quad (35)$$

$$\frac{dy}{dt} = 0.665 - 0.00212t \quad (36)$$

To determine the initial rate of water flux the derivative is evaluated at $t=0$, and $dy/dt = 0.665$ mg/min., equivalent to 0.665 μl/min. Then, normalizing the imbibition rate for time, membrane surface area and thickness, and the membrane permeability constant to water, $K\pi$ may be determined according to the following equation (37):

(37)

$$K\pi = 0.665 \, \mu l/\text{min} \times \left(\frac{60 \text{ min}}{\text{hr}}\right) \times \left(\frac{1 \text{ ml}}{1000 \, \mu l}\right)\left(\frac{0.008 \text{ cm}}{2.86 \text{ cm}^2}\right)$$

with $K\pi = 1.13 \times 10^{-4}$ cm²/hr. The $\pi$ value for NaCl was determined with a Hewlett Packard vapor pressure osmometer to be 345 atm ± 10%, and the K value for cellulose acetate used in this experiment calculated from NaCl imbibition values was determined to be $1.9 \times 10^{-7}$ cm²/hr atm.

Substituting these values into the calculated $K\pi$ expression, $(1.9 \times 10^{-7} \text{ cm}^2/\text{hr atm})(\pi) = 1.13 \times 10^{-4}$ cm²/hr gives $\pi = 600$ atm at $t=0$. As a method for evaluating the efficiency of a polymer with respect to duration of zero order driving force, the percent of water uptake was selected before the water flux values decreased to 90% of their initial values. The value of the slope for the equation of a straight line emanating from the axis will be equal to the initial value of dy/dt evaluated at $t=0$, with $(dy/dt)=0.665$ and the y intercept=0.359, which yields $y=0.665t+0.359$. In order to determine when the value of the cumulative water uptake is 90% below the initial rate, the following expression is solved for t:

$$0.9 = \frac{at^2 + bt + c}{bt + c} = \left(\frac{\Delta W}{w}\right)_{0.9} \quad (38)$$

$$\frac{-0.00106t^2 + 0.665t + 0.359}{0.665t + 0.359} = 0.9 \quad (39)$$

and solving for t, $$-0.00106t^2 + 0.0065t + 0.0359 = 0 \quad (40)$$

$$t = \frac{-0.0665 - [(0.0665)^2 - 4(-0.00106)(0.0359)]^{\frac{1}{2}}}{2(-0.00106)}$$

$t=62$ min and the weight gain is $-0.00106(62)^2 + (0.665)(62) + 0.359 = 38$ mg, with the initial sample weight=100 mg, thus $(\Delta w/w)_{0.9} \times 100 = 38\%$. The results are presented in FIG. 8 for a graphical representation of the values. Other methods available for studying the hydrogel solution interface include rheologic analysis, viscometric analysis, ellipsometry, contact angle measurements, electrokinetic determinations, infrared spectroscopy, optical microscopy, interface morphology and microscopic examination of an operative device.

The expression, "active agent," as used herein, denotes the beneficial drugs nifedipine, a calcium channel blocker; prazosin and its therapeutic salts, an antihypertensive; doxazosin and its therapeutic salts, an alpha-adrenoceptor antagonist; piroxicam, an anti-inflammatory, analgesic and antipyretic drug; prazosin and polythiazide, a combination for anti-hypertensive and diuretic activty; and polythiazide, for diuretic acitivty. The drugs are known in *Physician's Desk Reference*, 40th Ed., (1986), published by Medical Economics Co., Oradell, N.J.

The drug, where appropriate, can be in various forms, such as uncharged molecules, molecular complexes, pharmacologically acceptable salts such as hydrochloride, hydrobromide, sulfate, laurate, palmitate, phosphate, nitrate, borate, acetate, maleate, tartrate, oleate and salicylate. For acidic drugs, salts of metals, amines or organic cations; for example, quaternary ammonium salts can be used. Derivatives of drugs such as esters, ethers and amides can be used. Also, a drug that is water insoluble can be used in a form that is a water soluble derivative thereof to serve as a solute and, on its release from the device, is then converted by enzymes, hydrolyzed by body pH or other metabolic processes to the original biologically active form. The agent, including drug, can be present in the compartment with a binder, dispersant, wetting agent, suspending agent, lubricant and dye. Representative of these include suspending agents such as acacia, agar, calcium carrageenan, alginic acid, algin, agarose powder, collagen, colloidal magnesium silicate, pectin, gelatin and the like; binders like polyvinyl pyrrolidone, lubricants such as magnesium stearate; wetting agents such as fatty amines, fatty quaternary ammonium salts, and the like. The phrase drug formulation indicates the drug is present in the compartment accompanied by an optional osmagent, osmopolymer, a binder, and/or the like. The amount of beneficial agent in a device generally is about from 0.05 ng to 5 g or more, with individual devices containing, for example, 25 ng, 1 mg, 5 mg, 10 mg, 25 mg, 125 mg, 250 mg, 500 mg, 750 mg, 1.0 g, 1.2 g, and the like. The devices can be administered one, twice or thrice daily.

The solubility of a beneficial agent in the fluid can be determined by known techniques. One method consists of preparing a saturated solution comprising the fluid plus the agent as ascertained by analyzing the amount of agent present in a definite quantity of the fluid. A sample apparatus for this purpose consists of a test tube of medium size fastened upright in a water bath maintained at constant temperature and pressure, in which the fluid and agent are placed and stirred by a rotating glass spiral. After a given period of stirring, a weight of the fluid is analyzed and the stirring continued an additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may be not needed; if the agent has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in the *United States Public Health Service Bulletin,* No. 67 of the Hygienic Laboratory; *Encyclopedia of Science and Technology,* Vol. 12, pp 542 to 556, (1971) published by McGraw-Hill, Inc.; and *Encyclopedia Dictionary of Physics,* Vol. 6, pp 547 to 557, (1962) published in Pergamon Press, Inc.

The osmotic device of the invention is manufactured by standard techniques. For example, in one embodiment the beneficial agent is mixed with an osmagent and osmopolymer, and pressed into a solid possessing dimensions that correspond to the internal dimensions of the compartment adjacent to the passageway; or the beneficial agent and other formulation forming ingredients and a solvent are mixed into a solid or a semisolid by conventional methods such as ballmilling, calendering, stirring or rollmilling, and then pressed into a preselected shape. Next, a layer of a composition comprising an osmagent and an osmopolymer is laced in contact with the layer of beneficial agent formulation, and the two layers surrounded with a semipermeable wall. The layering of the beneficial agent composition and the osmagent/osmopolymer can be accomplished by conventional two-layer tablet press techniques. The wall can be applied by molding, spraying, pan coating, or dipping the pressed shapes into wall-forming materials. Another and presently preferred technique that can be used for applying the wall is the air suspension coating procedure. This procedure consists in suspending and tumbling the pressed compositions in a current of air and a wall forming composition until the wall surrounds and coats the two pressed compositions. The air suspension procedure is described in U.S. Pat. No. 2,799,241; *J. Am. Pharm. Assoc.,* Vol. 48, pp 451 to 459 (1979); and, ibid, Vol. 49 pp 82 to 84 (1960). Other standard manufacturing procedures are described in *Modern Plastics Encyclopedia,* Vol. 46, pp 62 to 70 (1969): and in *Pharmaceutical Science,* by Remington, 14th Ed., pp 1626 to 1978 (1970), published by Mack Publishing Co., Easton, PA.

Exemplary solvents suitable for manufacturing the laminates and laminae include inert inorganic and organic solvents that do not adversely harm the materials and the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclooctane, benzene, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DESCRIPTION OF EXAMPLES

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

Osmotic delivery systems for administering the therapeutically beneficial drug doxazosin are provided by the invention comprising a first composition, which first composition comprises: from 1 to 25 mg of a member selected from the group consisting of doxazosin and its pharmaceutically acceptable salts; from 250 to 325 mg of polyethylene oxide selected from the group consisting of from 0 to 275 mg of a polyethylene oxide having a molecular weight of about 100,000 and from 0 to 275 mg of a polyethylene oxide having a molecular weight of about 200,000; from 10 to 30 mg of a hydroxypropylmethylcellulose having an average molecular weight of about 11,300; from 0 to 5 mg of ferric oxide and from 0 to 10 mg of magnesium stearate; a second composition which second composition comprises from about 110 to 140 mg of a polyethylene oxide selected from the group consisting of a polyethylene oxide having an average molecular weight of about 5,000,000 and a polyethylene oxide having an average molecular weight of about 7,500,000; from 5 to 25 mg of a hydroxypropylmethylcellulose having an average molecular weight of about 11,300; from 0 to 5 mg of ferric oxide; from 40 to 70 mg of sodium chloride; and, from 0 to 10 mg of magnesium stearate; and a wall comprising from 30 to 50 mg of cellulose acetate having an acetyl content selected from the group consisting of 32% and 39.8%, and from 1 to 10 mg of polyethylene glycol having an average molecular weight of about 3350 to 4000. The systems comprises at least one exit passageway.

EXAMPLE 2

An osmotic delivery system for administering doxazosin, an alpha-adrenoceptor antagonist that lowers blood pressure by reducing peripheral resistance, and is a useful antihypertensive, was manufactured as described herein. The following materials were blended and wet granulated in a mixer: 248.5 g of doxazosin mesylate; 3795 g Polyox ® N-10, a polyethylene oxide polymer having a molecular weight of about 100,000; 2530 g of Polyox ® N-80, a polyethylene oxide polymer having a molecular weight of about 200,000; and 350 g of a hydroxypropylmethylcellulose having an average molecular weight of about 11,300. The wet granulation was carried out using denatured anhydrous ethanol as the granulating fluid. The wet granules were passed through a 7 mesh screen and dried overnight in a forced air oven. Then, the dried granules were sized through a 10 mesh screen and then 1% magnesium stearate was added thereto in the mixer.

Next, the following materials were blended and wet granulated in a mixer: 3225 g of Polyox ® Coagulant, a polyethylene oxide having a molecular weight of about 5,000,000; 1450 g of sodium chloride; 250 g of hydroxypropylmethylcellulose having a molecular weight of about 11,300 and 50 g of ferric oxide. The granulation was carried out using denatured ethanol as the granulating fluid. The wet granules were passed through a 10 mesh screen and dried overnight in a forced air oven. The dried granules were re-sized through a 12 mesh screen and then 0.5% magnesium stearate was added thereto in the mixer.

The number of compartment bilayers were compressed on a Manesty ® Layerpress. The drug layer contained 4.4 mg of doxazosin. The total weight of the drug layer and the push layer was 250 mg. The compartment forming layers were coated with 21 mg of a cellulosic rate controlling wall; next the osmotic devices were drilled with a laser for providing a 20 mil orifice on the drug side. The osmotic systems were dried in an oven for 3 days. The drug layer weighed 150 mg, the osmotic push layer weighed 100 mg, and the semipermeable wall comprised 90% cellulose acetate having an acetyl content of 39.8% and 10% polyethylene glycol 3500. The wall forming solution contained 4% solids and the coating solvents comprised 90% methylene chloride and 10% methanol (w/w). The device exhibited a rate of release of 0.48 mg of doxazosin per hour.

EXAMPLE 3

The procedure of Example 2 was repeated to provide osmotic devices containing 3.3 mg of doxazosin. In these devices, the drug layer weighed 112.5 mg, and the osmotic expandable layer weighed 75 mg. The wall weighed 18 mg and it comprised 90% cellulose acetate having an acetyl content of 39.8% and 10% polyethylene glycol 3350. The devices had a 20 mil drug dispensing exit passageway and they released doxazosin at the rate of 0.35 mg per hour.

EXAMPLE 4

The procedure of Example 2 was repeated to provide osmotic devices comprising a drug layer consisting of 4.4 mg of doxazosin. The drug layer weighed 150 mg and the osmotic expandable layer weighed 100 mg. The wall weighed 23 mg and consists essentially of 95% of cellulose acetate having an acetyl content of 39.8% and 5% polyethylene glycol 3350. The device had a 20 mil aperture and release doxazosin at the rate of 0.25 mg per hr.

EXAMPLE 5

Figure 9:
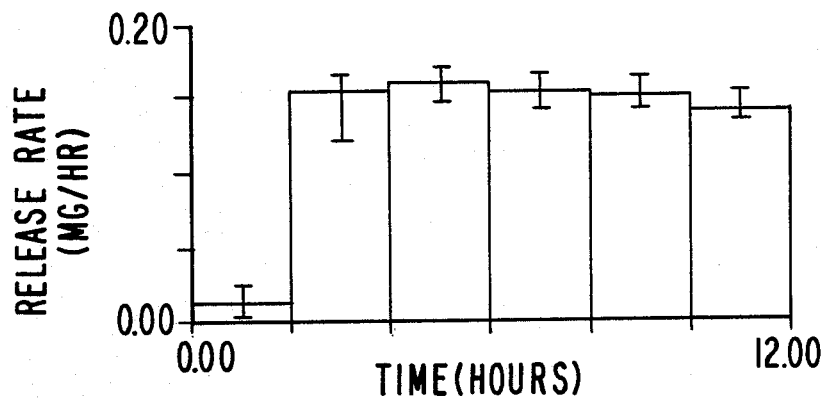
FIG. 9 is a graph depicting the amount of doxazosin released per hour from a delivery device.
Figure 10:
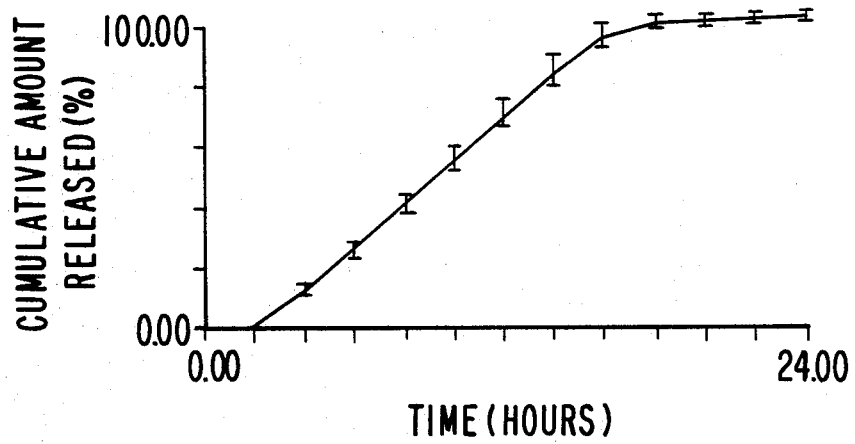
FIG. 10 is a graph depicting the cumulative amount of doxazosin released over a prolonged period of time.

The procedures of Example 2 to 4 were followed in this example for providing a series of osmotic dispensing devices as follows: a device comprising a first composition which composition comprises 2.4 mg of doxazosin mesylate, 83 mg of polyethylene oxide having 100,000 average molecular weight, 56 mg of polyethylene oxide having a 200,000 average molecular weight, 7.5 mg of hydroxypropylmethylcellulose having a 11,300 molecular weight, 0.015 mg of ferric oxide, and 1.5 mg of magnesium stearate, a second composition which composition comprises 64.5 mg of polyethylene oxide having an average 7,500,000 molecular weight, 29 mg of sodium chloride, 5 mg of hydroxypropylmethylcellulose having a 11,300 average molecular weight, 1 mg of ferric oxide, and 0.5 mg of magnesium stearate; a semipermeable wall comprising 23.5 mg of cellulose acetate having a 39.8% acetyl content, and 2 mg of polyethylene glycol having a 3350 molecular weight; an exit orifice having a diameter of 0.64 mm; and which osmotic device delivers 85% of the drug in 12 hrs; an osmotic device comprising 4.8 mg of doxazosin mesylate, 83 mg of polyethylene oxide having a 100,000 molecular weight, 56 mg of polyethylene oxide having a 200,000 molecular weight, 7.5 mg of hydroxypropylmethylcellulose having a 11,300 molecular weight 0.015 mg of ferric oxide, and 1.5 mg of magnesium stearate, a second composition which second composition comprises 64.5 mg of polyethylene oxide having a 7,500,000 molecular weight 29 mg of sodium chloride, 5 mg of hydroxypropylmethylcellulose having a 11,300 molecular weight, 1 mg of ferric oxide and 0.5 mg of magnesium stearate; a semipermeable wall comprising 23.5 mg of cellulose acetate having a 39.8% acetyl content, and 2 mg of polyethylene glycol having a 3350 molecular weight; an exit orifice of 0.64 mm, and wherein the device delivers 85% of the drug in 12 hrs; and an osmotic device comprising a first composition, which first composition comprises 9.6 mg of doxazosin mesylate, 166 mg of polyethylene oxide having a 100,000 molecular weight, 111 mg of polyethylene oxide having a 200,000 molecular weight, 15 mg of hydroxypropylmethylcellulose having a 11,300 molecular weight, 0.03 mg of ferric oxide, and 3 mg of magnesium stearate, and a second composition which second composition comprises 129 mg of polyethylene oxide having a 7,500,000 molecular weight, 58 mg of sodium chloride, 10 mg of hydroxypropylmethylcellulose having a 11,300 molecular weight, 2 mg of ferric oxide and 1 mg of magnesium stearate; a semipermeable wall comprising 37 mg of cellulose acetate having a 39.8% acetyl content, and 3 mg of polyethylene glycol; which device has a passageway that delivers 85% of the doxazosin salt in 12 hours. Accompanying FIG. 9 illustrates the release rate in mg per hour, from a device comprising 2.2 mg of drug doxazosin. The vertical bars indicate the minimum and maximum variation in release from 10 devices. The mean zero-order release rate from the device is 0.152 mg/hr. FIG. 10 depicts the cumulative amount released over a prolonged period of time, 24 hrs. The vertical bars represent the maximum and minimum release rate variation for 10 devices. The device initially comprises 8.80 mg of doxazosin mesylate, and had a mean zero-order release rate of 0.56 mg per hr.

EXAMPLES 6 TO 8

Figure 11:
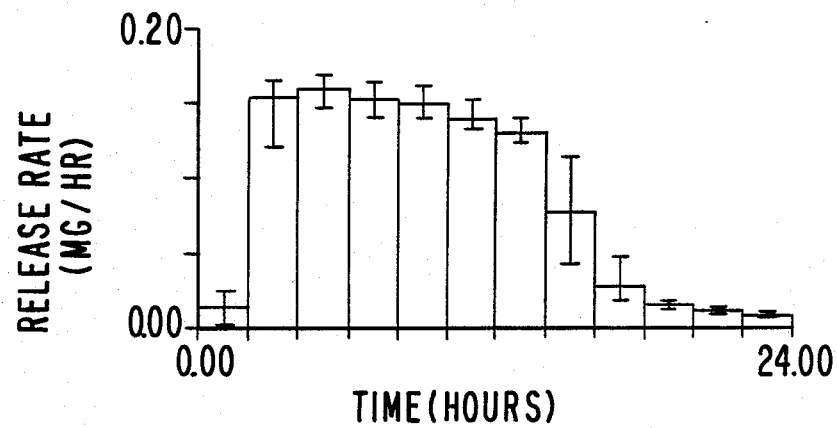
FIGS. 11 to 16 illustrate various release rate patterns provided by the invention.
Figure 12:
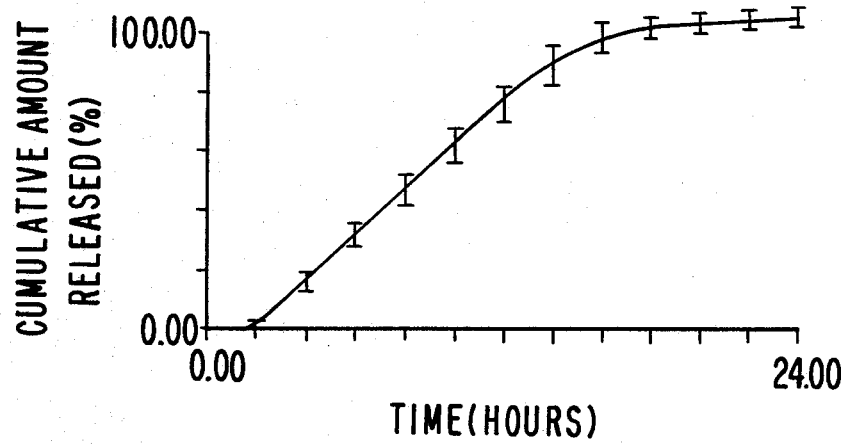
Figure 13:
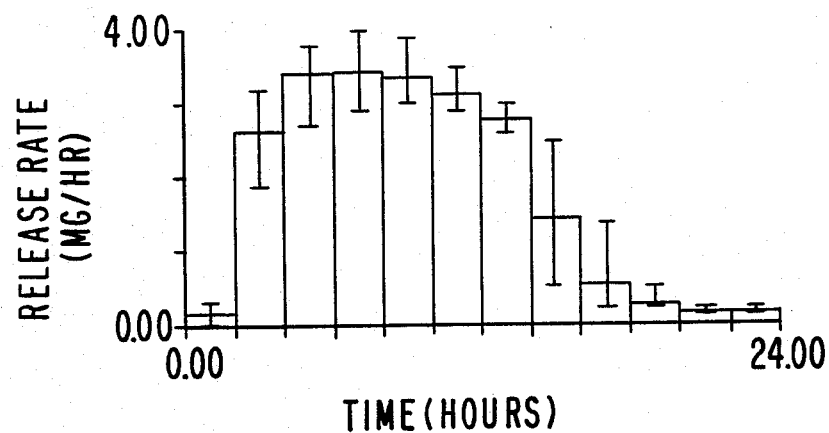
Figure 14:
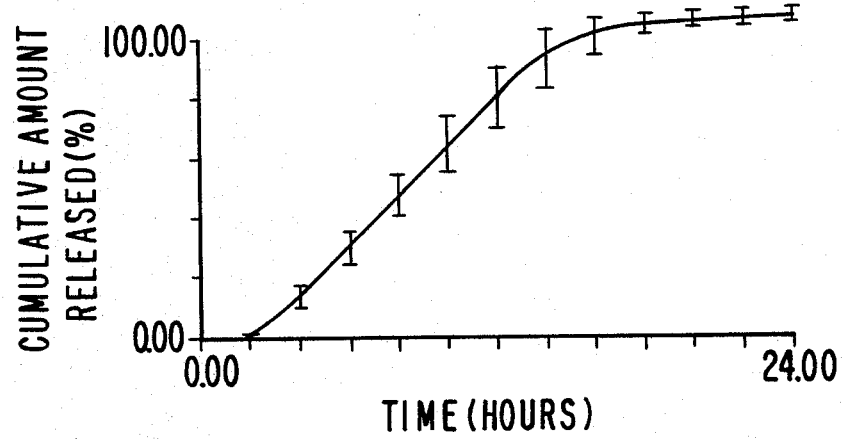
Figure 15:
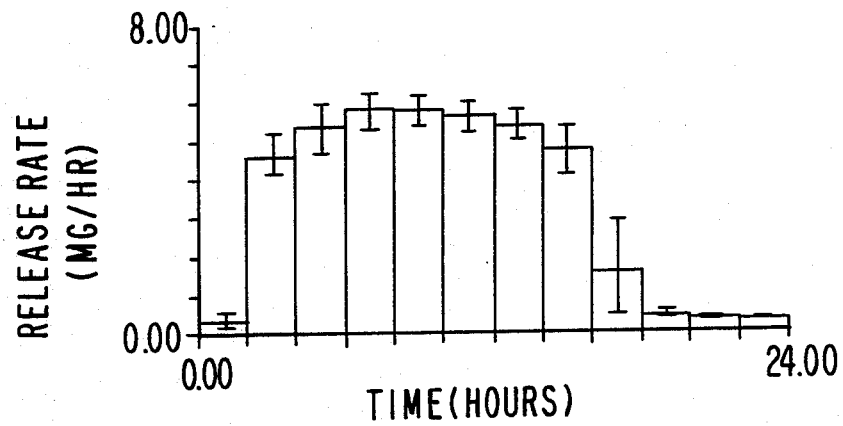
Figure 16:
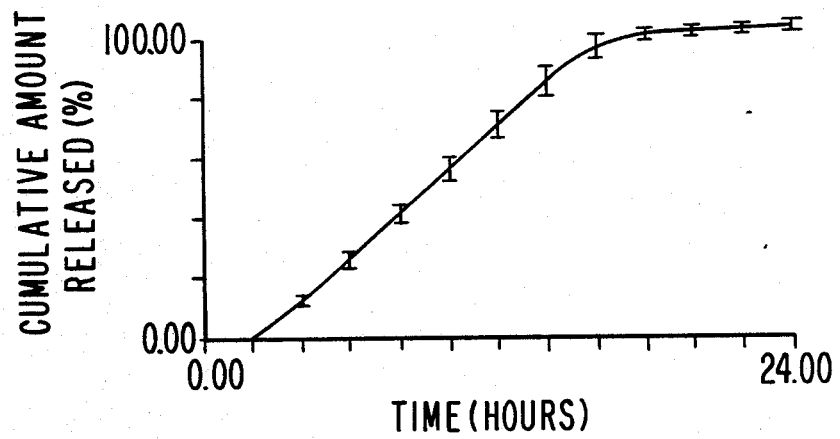

Following the above procedures oral dosage forms are prepared comprising: (A) a drug layer comprising doxazosin mesylate present as 1.47 wt % doxazosin and 0.31 wt % mesylate, 55.27 wt % Polyox ® N-10, 36.85 wt % Polyox ® N-80, 5 wt % hydroxypropyl methylcellulose E-5, 0.1 wt % yellow ferric oxide, 1 wt % magnesium stearate; a push layer comprising 64.50 wt % Polyox ® WSR-303, 29 wt % sodium chloride, 5 wt % hydroxypropyl methylcellulose, 1 wt % red ferric oxide, and 0.5 wt % magnesium stearate; a wall comprising 92.5 wt % cellulose acetate having an acetyl content of 39.8% and 7.5 wt % polyethylene glycol 3340; an orifice of 20 mils; a release rate in mg/hr as seen in FIG. 11 and a cumulative amount released as seen in FIG. 12; (B) an oral dosage form with a drug layer comprising doxazosin mesylate present as 2.93 wt % doxazosin, 0.62 wt % mesylate, 54.26 wt % Polyox ® N-10, 36.18 wt % Polyox ® N-80, 5 wt % hydroxypropyl methylcellulose E-5, 0.01 wt % red ferric oxide, 1.00 wt % magnesium stearate; a push layer comprising 64.50 wt % Polyox ® WSR 303, 29.0 wt % sodium chloride, 5 wt % hydroxypropyl methylcellulose E-5, 1.0 wt % ferric oxide, and 0.5 wt % magnesium stearate; a wall comprising 92.50 wt % cellulose acetate having an acetyl content of 39.8% and 7.5 wt % polyethylene glycol 3350; an orifice having a diameter of 0.51 mm; a release rate as depicted in FIG. 13 and a cumulative amount released as seen in FIG. 14; and (C) an oral dosage form having a drug layer comprising doxazosin mesylate present as 2.93 wt % doxazosin, 0.62 wt % mesylate, 54.26 wt % Polyox ® N-10, 36.18 wt % Polyox ® N-80, 5.0 wt % hydroxypropyl methylcellulose E-5, 0.01 wt % red ferric oxide, 1 wt % magnesium stearate; a push layer comprising 64.50 wt % hydroxypropyl methylcellulose E-5, 1 wt % red ferric oxide, 0.5 wt % magnesium stearate; a wall comprising 92.5 wt % cellulose acetate having a molecular weight of 39.8%, and 7.5 wt % polyethylene glycol 3350; the drug layer weighed 300 mg; the orifice has a diameter of 0.64 mm; the release rate is present in FIG. 15 and the cumulative release is given in FIG. 16.

EXAMPLE 9

The beneficial drug doxazosin is administered to an animal host, such as a human, at a controlled and a continuous rate according to the method of administering the drug provided by the invention. The method comprises the steps of: (A) admitting orally into the gastrointestinal tract of a human delivery system comprising: (1) a wall comprising in at least a part a semipermeable composition permeable to the passage of an exterior fluid present in the environment of use and substantially impermeable to the passage of drug, which wall surrounds and forms; (2) an internal compartment; (3) a first composition in the compartment, said first composition comprising doxazosin mesylate and an osmopolymer composition that exhibits an osmotic pressure gradient across the wall against an external fluid; (4) a second composition in the compartment, said second composition comprising an osmopolymer and an osmagent that exhibit an osmotic pressure gradient across the wall against an external fluid; (5) a passageway in the wall communicating with the first composition and the exterior of the osmotic device for delivering the beneficial drug doxazosin through the passageway to the human; and (B) administering a therapeutically effective amount of doxazosin to the human, by imbibing fluid through the semipermeable wall into the osmotic system to form a dispensable first composition comprising doxazosin, and a second expanding composition, whereby the drug doxazosin is administered by the combined actions of the first and second compositions through the passageway to the human over time.

The novel osmotic system of this invention uses dual means for the attainment of precise release rate of drugs that are difficult to deliver in the environment of use, while simultaneously maintaining the integrity and the character of the system. While there has been described and pointed out features and advantages of the invention as applied to the presently preferred embodiments, those skilled in the dispensing art will appreciate that various modifications, changes, additions, and omissions in the system illustrated and described can be made without departing from the spirit of the invention.

We claim:

1. An osmotic device for administering a therapeutically effective amount of doxazosin to an environment of use, the osmotic device comprising:
   (a) a wall comprising in at least a part a cellulose acetate composition permeable to the passage of an exterior fluid, which wall surrounds and forms;
   (b) a compartment;
   (c) a first composition in the compartment, said first composition comprising from 1 to 25 mg of doxazosin, from 250 to 325 mg of polyethylene oxide, and from 10 to 30 mg of hydroxypropylmethylcellulose;
   (d) a second composition in the compartment, said second composition comprising from 110 to 140 mg of polyethylene oxide, from 40 to 70 mg of sodium chloride, and from 5 to 25 mg of hydroxypropylmethylcellulose; and,
   (e) at least one passageway in the wall communicating with the compartment and the exterior of the device for delivering the therapeutic drug doxazosin to the environment of use.

2. The osmotic device for administering doxazosin according to claim 1, wherein the first composition comprises 2.4 mg of doxazosin mesylate, 83 mg of polyethylene oxide having a 100,000 molecular weight, 56 mg of polyethylene oxide having a 200,000 molecular weight, and 7.5 mg of hydroxypropylmethylcellulose having a 11,300 molecular weight.

3. The osmotic device for administering doxazosin according to claim 1, wherein the first composition comprises 4.8 mg of doxazosin mesylate, 83 mg of polyethylene oxide having a 100,000 molecular weight, 56 mg of polyethylene oxide having a 200,000 molecular weight, and 7.5 mg of hydroxypropylmethylcellulose having a 11,300 molecular weight.

4. The osmotic device for administering doxazosin according to claim 1, wherein the first composition comprises 9.6 mg of doxazosin mesylate, 166 mg of polyethylene oxide having a 100,000 molecular weight, 111 mg of polyethylene oxide having a 200,000 molecular weight and 15 mg of hydroxypropylmethylcellulose having a 11,300 molecular weight.

5. The osmotic device for administering doxazosin according to claim 1, wherein the second composition comprises 64.5 mg of polyethylene oxide having a 7,500,000 molecular weight, 29 mg of sodium chloride, and 5 mg of hydroxypropylmethylcellulose having a 11,300 molecular weight.

6. The osmotic device for administering doxazosin according to claim 1, wherein second composition comprises 129 mg of polyethylene oxide having a 7,500,000 molecular weight, 58 mg of sodium chloride, and 10 mg of hydroxypropylmethylcellulose having a 11,300 molecular weight.

7. The osmotic device for administering doxazosin according to claim 1, wherein the first composition comprises about 2.6 mg of doxazosin mesylate.

8. The osmotic device for administering doxazosin according to claim 1, wherein the first composition comprises about 5.3 mg of doxazosin mesylate.

9. The osmotic device for administering doxazosin according to claim 1, wherein the first composition comprises about 10.6 mg of doxazosin mesylate.

10. The osmotic device for administering doxazosin according to claim 1, wherein the second composition comprises 64.5 mg of polyethylene oxide having a 5,000,000 molecular weight, 29 mg of sodium chloride, and 5 mg of hydroxypropylmethylcellulose having a 11,300 molecular weight.

* * * * *